US 6,651,405 B1

(12) United States Patent
Vetter et al.

(10) Patent No.: US 6,651,405 B1
(45) Date of Patent: Nov. 25, 2003

(54) APPARATUS FOR MOUNTING A TIP CAP ON A SYRINGE SUBASSEMBLY

(75) Inventors: Udo J. Vetter, Ravensburg (DE); Joachim Oliveira, Lindenberg (DE); Hubert Sauter, Weingarten (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 205 days.

(21) Appl. No.: 09/698,937

(22) Filed: Oct. 27, 2000

(30) Foreign Application Priority Data

Oct. 30, 1999 (DE) .......................... 199 52 358

(51) Int. Cl.[7] .............................. B65B 7/00; B67B 3/06
(52) U.S. Cl. ............................................ 53/285; 53/309
(58) Field of Search ................................. 604/187, 188, 604/192, 263, 199; 128/898, 919; 422/25–28, 102; 264/232, 238, 250, 136.15, 632; 141/1, 5, 11; 413/2, 3, 45, 26, 47, 48–52; 403/12; 137/15.01; 53/285–378.3, 389.1–389.5

(56) References Cited

U.S. PATENT DOCUMENTS

| 3,791,009 A | * | 2/1974 | Gess | 29/775 |
| 4,096,683 A | * | 6/1978 | McMickle, Jr. | 53/244 |
| 4,271,587 A | * | 6/1981 | Shields | 29/809 |
| 4,718,463 A | * | 1/1988 | Jurgens et al. | 422/25 |
| 5,597,530 A | * | 1/1997 | Smith et al. | 422/102 |
| 5,620,425 A | * | 4/1997 | Heffernan et al. | 128/898 |
| 5,687,542 A | * | 11/1997 | Lawecki et al. | 264/232 |
| 6,189,292 B1 | * | 2/2001 | Odell et al. | 141/1 |

* cited by examiner

Primary Examiner—Brian L. Casler
Assistant Examiner—Catherine Serke
(74) Attorney, Agent, or Firm—Herbert Dubno; Andrew Wilford

(57) ABSTRACT

An apparatus for mounting a tip cap having a maximum diameter over a syringe subassembly having a syringe body with an end carrying a needle has a holder holding the subassembly with the needle substantially on an axis and a tubular guide having a feed passage generally centered on the axis adjacent the holder, of an inside diameter greater than the maximum tip-cap diameter, and open toward the holder. A stop can move between a blocking position between the guide and the holder and an unblocking position offset therefrom. The tip cap is fed through the passage to a position arrested on the stop in the blocking position thereof. A nozzle opening into the passage injects pressurized gas into the passage and thereby spins the tip cap in the passage about the axis. The stop can then be moved from the blocking into the unblocking position for displacing the spinning tip cap from the guide onto the syringe subassembly in the holder. The nozzle opens tangentially into the passage.

11 Claims, 3 Drawing Sheets

APPARATUS FOR MOUNTING A TIP CAP ON A SYRINGE SUBASSEMBLY

FIELD OF THE INVENTION

The present invention relates to the manufacture of syringes. More particularly this invention concerns an apparatus for fitting a tip or needle cap to a syringe subassembly formed by a syringe body carrying a needle.

BACKGROUND OF THE INVENTION

In the production of a syringe the needle or cannula is typically mounted by gluing to the end of a stepped tubular syringe body normally made of glass or plastic. Then a tip cap is fitted over the needle end of the body to preserve sterility of the needle and protect users from its sharp point. The tip cap is formed normally as a tapered sleeve centered on an axis and having a small-diameter closed end and a large-diameter open end from which a rim projects radially. It is made of a stiff elastomer so that it can be force-fitted over the needle end of the syringe body.

The automatic machine that fits the tip cap to the syringe subassembly comprised of the syringe body and its needle typically comprises a holder that supports the syringe subassembly and a system for feeding the caps, open end first, axially over the needle end of the syringe subassembly. The feed system typically comprises a tubular guide whose outer end is connected to a supply of the tip caps and whose inner end opens coaxially with the syringe in the holder.

The problem with such an arrangement is that the cap is normally not centered in the guide tube, instead lying against one of its walls. In fact the cap, whose upper end is quite small, normally is canted inside this guide tube. If the needle tip catches on the inner surface of such a nonstraight cap when it is fitted thereover, it will pierce through it. This will of course impair the sterility of the finished assembly and leave the needle tip exposed which presents a hazard to personnel handling the syringe. In addition the needle often excises and holds a tiny plug of the cap when it catches on it, even if it comes free and does not pierce through it, and during subsequent use this plug of the end-cap material can actually be injected into a patient. The result is therefore a defective or dangerous syringe.

OBJECTS OF THE INVENTION

It is therefore an object of the present invention to provide an improved apparatus for fitting a tip cap to a syringe subassembly.

Another object is the provision of such an improved apparatus for fitting a tip cap to a syringe subassembly which overcomes the above-given disadvantages, that is which ensures that the caps are fitted coaxially over the end of the needle subassembly.

SUMMARY OF THE INVENTION

An apparatus for mounting a tip cap having a maximum diameter over a syringe subassembly having a syringe body with an end carrying a needle has according to the invention a holder holding the subassembly with the needle substantially on an axis and a tubular guide having a feed passage generally centered on the axis adjacent the holder, of an inside diameter greater than the maximum tip-cap diameter, and open toward the holder. A stop can move between a blocking position between the guide and the holder and an unblocking position offset therefrom. The tip cap is fed through the passage to a position arrested on the stop in the blocking position thereof. A nozzle opening into the passage injects pressurized gas into the passage and thereby spins the tip cap in the passage about the axis. The stop can then be moved from the blocking into the unblocking position for displacing the spinning tip cap from the guide onto the syringe subassembly in the holder.

Thus with this system the tip cap is centered in the passage by the gas, normally compressed air. According to the invention the nozzle opens tangentially into the passage. This imparts excellent spin to the tip cap so that when the stop is withdrawn and, if necessary, the holder and guide are axially moved toward each other, it fits coaxially over the needle onto the syringe body. Thereafter standard devices are used to press the tip cap snugly into place on the syringe body.

In accordance with the invention for most effective spinning two such nozzles open tangentially into the passage diametrally offset from each other.

The stop according to the invention is a plate movable transversely of the axis. It forms a slot at the axis. This plate can have a pair of oppositely movable parts together forming the slot. Alternately the stop is an iris, like a camera shutter. In another system the stop is at least one plate pivotal about an axis lying in a plane perpendicular to the axis between the blocking and unblocking positions.

The passage according to the invention is cylindrical and the axis is upright.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
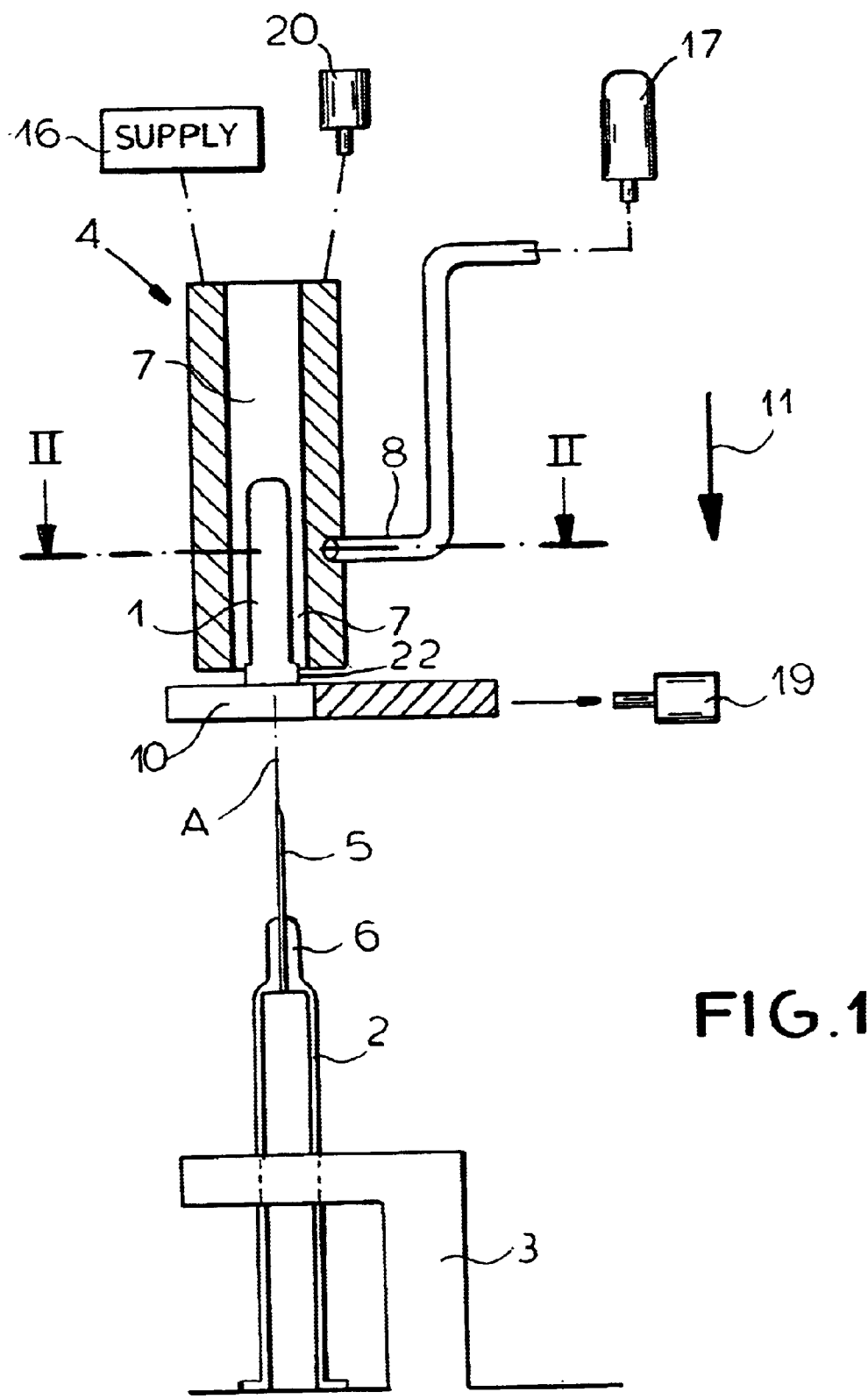
FIG. 1 is a partly diagrammatic side view of the apparatus according to the invention.

As seen in FIG. 1 a tip cap 1 is axially symmetrical and has a lower end formed with a radially outwardly projecting rim 22. It is intended to be mounted on a small-diameter needle end 6 of a larger-diameter syringe body 2 fitted at this end 6 with a needle 5 and held in a holder 3 that may also hold a plurality of other such syringe subassemblies 2, 5. The syringe body 2 and needle 5 are centered on an upright axis A.

Figure 3:
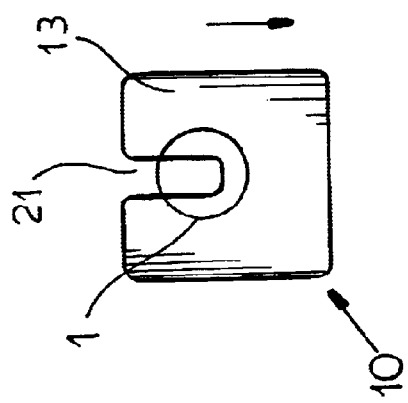
FIG. 3 is a top view of a detail of FIG. 1.

The caps 1 are fed in from a means constituted by a supply 16 through a tubular guide 4 having a lower end forming a cylindrical passage 7 centered on the axis A but of an inside diameter somewhat greater than a maximum outside diameter of the cap 1 measured at its rim 22. Underneath the lower end or mouth of the passage 7 is a stop 10 formed as a plate 13 (FIG. 3) having a narrow slot 21 and displaceable in a horizontal plane perpendicular to the axis A by an actuator 19 forming stop-moving means. This slot 21 is wide enough to pass the narrow end 6 of the body 2, but smaller than the diameter of the cap 1 as shown in FIG. 3. Thus the stop plate 13 can prevent the cap 1 from falling out of the bottom of the guide passage 7.

Figure 2:
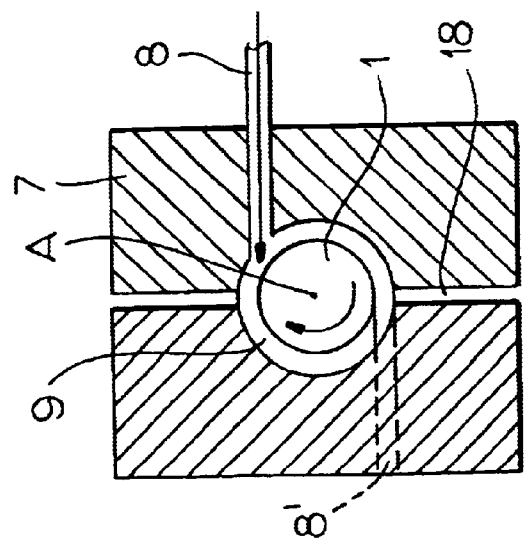
FIG. 2 is a section taken along line II—II of FIG. 1.

According to the invention as shown in FIG. 2 a nozzle passage 8 connected to a pressurized-gas source 17 (FIG. 1) and lying in a plane perpendicular to the axis A opens tangentially into a space 9 defined between the cap 1 and an inner surface of the passage 7 and constitutes means for spinning the cap 1. The passage 7 is open at a pair of diametrally opposite slots 18 that allow the incoming air to escape, and may have a second such nozzle passage 8' diametrally opposite the passage 8. The incoming air flow will normally set the cap 1 loosely received in the passage 7 into high-speed rotation about the axis A and will automatically center the cap 1 on the axis A.

Once thus centered the stop 10 is withdrawn and, if necessary, the syringe subassembly 2, 5 and guide 7 are moved axially together as shown by arrow 11 by means constituted by an actuator such as shown at 20 connected to the guide 4. The cap 1 will move out of the lower end of the guide passage 7, both by gravity and by the force of the air behind it, and will drop coaxially atop the syringe body 2. The spin imparted to it will keep it aligned with the axis A, as the rifling in a gun barrel spins its projectile to keep it on track.

Figure 4:
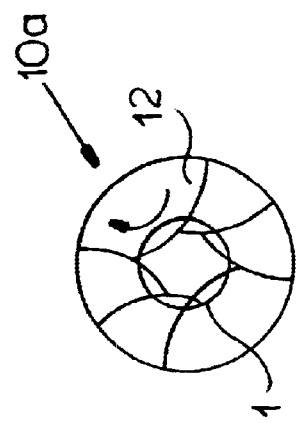
FIGS. 4 and 5 are views like FIG. 2 showing alternative systems according to the invention.
Figure 5:
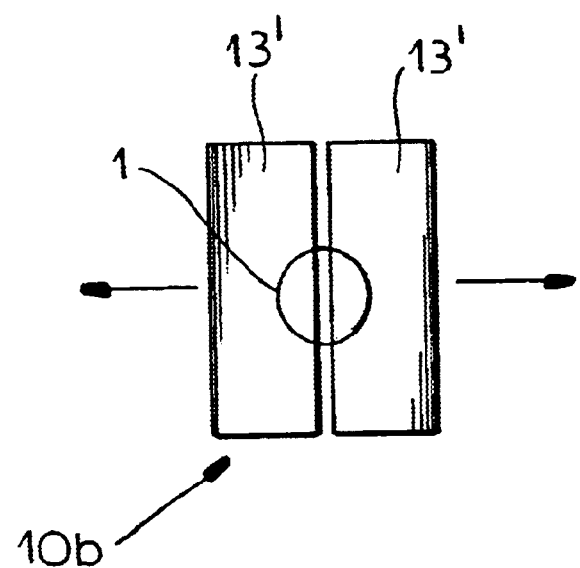
Figure 6:
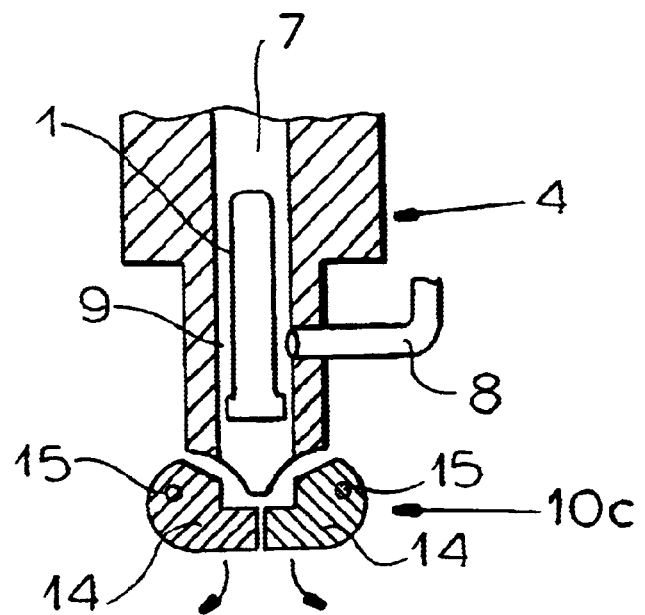
FIG. 6 is a side view of another variant on the invention.

According to the invention as shown in FIG. 4 the stop 10a is an iris 12 like that used in a camera shutter. Alternately a pair of oppositely slidable plates 13' can be used in a stop 10b as shown in FIG. 5. FIG. 6 shows a stop 10c comprises of a pair of members 14 flanking the axis A and pivotal about respective axes 15 symmetrically flanking the axis A and lying in a plane perpendicular thereto. They can be pivoted down and out to allow the cap 1 to drop out of the passage 7.

Once the tip cap 1 has been dropped down onto the end 6 of the body 2, other unillustrated means serve to push it tightly into place. Normally the syringe subassembly 5, 6 is axially reciprocated briefly to seat the tip cap 1, then a fork fits over it to press it tightly into place.

We claim:

1. An apparatus for mounting a tip cap having a maximum diameter over a syringe subassembly having a syringe body with an end carrying a needle, the apparatus comprising:

a holder holding the subassembly with the needle substantially on an axis;

a tubular guide having a feed passage generally centered on the axis adjacent the holder, of an inside diameter greater than the maximum tip-cap diameter, and open toward the holder;

a stop movable between a blocking position between the guide and the holder and an unblocking position offset therefrom;

means for feeding the tip cap through the passage to a position arrested on the stop in the blocking position thereof;

means including a nozzle opening transversely of the axis into the passage for injecting pressurized gas into the passage and spinning the tip cap in the passage about the axis so as to center the tip cap on the axis; and means for moving the stop from the blocking into the unblocking position for displacing the tip cap from the guide onto the syringe subassembly in the holder.

2. The tip-cam mounting apparatus defined in claim 1 wherein the nozzle opens tangentially into the passage.

3. The tip-cam mounting apparatus defined in claim 2 wherein two such nozzles open tangentially into the passage diametrally offset from each other.

4. The tip-cam mounting apparatus defined in claim 1 wherein the stop is a plate movable transversely of the axis.

5. The tip-cam mounting apparatus defined in claim 4 wherein the stop forms a slot at the axis.

6. The tip-cam mounting apparatus defined in claim 5 wherein the plate has a pair of oppositely movable parts together forming the slot.

7. The tip-cam mounting apparatus defined in claim 2 wherein the stop is an iris.

8. The tip-cam mounting apparatus defined in claim 2 wherein the stop is at least one plate pivotal about an axis lying in a plane perpendicular to the axis between the blocking and unblocking positions.

9. The tip-cam mounting apparatus defined in claim 2 wherein the passage is cylindrical.

10. The tip-cam mounting apparatus defined in claim 2 wherein the axis is upright.

11. The tip-cam mounting apparatus defined in claim 2, further comprising means for moving the holder and guide axially toward each other for fitting the tip cap over the needle.

* * * * *